(12) United States Patent
Mustacich et al.

(10) Patent No.: US 6,223,584 B1
(45) Date of Patent: May 1, 2001

(54) SYSTEM AND METHOD FOR VAPOR CONSTITUENTS ANALYSIS

(75) Inventors: Robert V. Mustacich; John P. Richards, both of Santa Barbara, CA (US)

(73) Assignee: RVM Scientific, Inc., Santa Barbara, CA (US)

( * ) Notice: Subject to any disclaimer, the term of this patent is extended or adjusted under 35 U.S.C. 154(b) by 0 days.

(21) Appl. No.: 09/321,110

(22) Filed: May 27, 1999

(51) Int. Cl.[7] .............................. G01N 1/00; B01D 53/02; B01D 59/44
(52) U.S. Cl. ............... 73/23.41; 73/863.11; 250/288; 95/82; 96/102
(58) Field of Search ............................. 73/23.41, 23.42, 73/863.11, 382 R; 250/288; 95/82; 96/102, 104

(56) References Cited

U.S. PATENT DOCUMENTS

| | | |
|---|---|---|
| 4,180,389 * | 12/1979 | Paul ................................. 95/11 |
| 5,014,541 | 5/1991 | Sides et al. . |
| 5,123,276 * | 6/1992 | Hartman et al. .................... 73/23.41 |
| 5,611,846 | 3/1997 | Overton et al. . |
| 6,112,602 * | 9/2000 | Mitra ................................. 73/863.12 |

* cited by examiner

*Primary Examiner*—Hezron Williams
*Assistant Examiner*—Jay L. Politzer
(74) *Attorney, Agent, or Firm*—Rosenberg, Klein & Lee

(57) ABSTRACT

A system for analysis of vapor constituents in a gaseous and/or liquid media includes an analyzing gas chromatographic unit, an in-line preconcentrator assembly having a trap housing, an adsorbent material received in the trap housing, and a transfer line unit couplable to the trap housing and directly connected to the analyzing unit. Carrier mechanism drives the trap housing with respect to the transfer line unit linearly or along an arc trajectory. When the trap housing is displaced from the transfer line unit, the media surrounding the trap housing is forced inside of the trap housing by a pump and vapor constituents are adsorbed on the adsorbent material within the trap housing. When the trap housing is moved in pressure tight engagement with the transfer line unit, the adsorbent material is heated to release the vapor constituents from the adsorbent material.

28 Claims, 15 Drawing Sheets

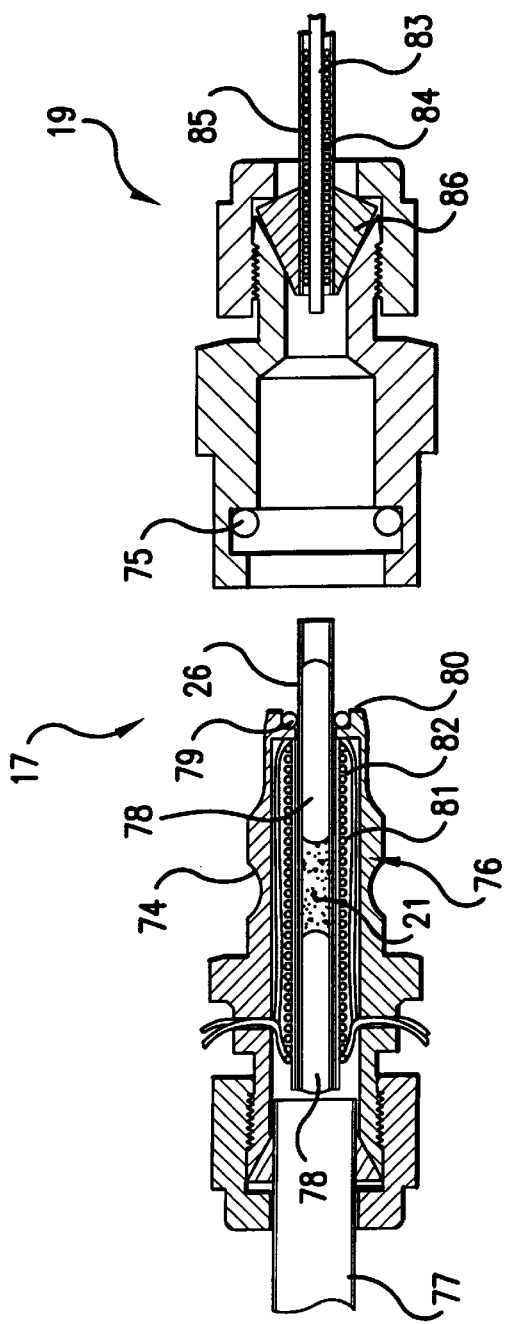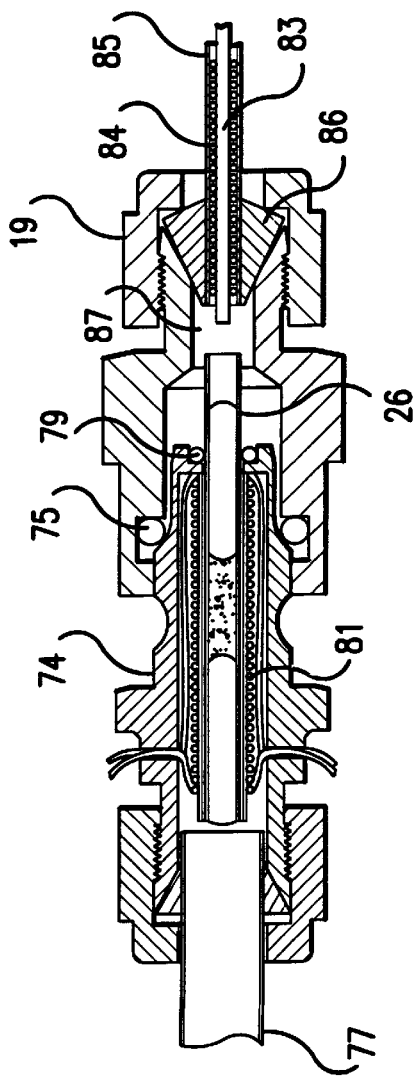
FIG.7
FIG.8

SYSTEM AND METHOD FOR VAPOR CONSTITUENTS ANALYSIS

The development of this invention was funded by the Government through Prime Contracts DNA001-95-C-0195 and DSWA01-97-C-0110 with the Defense Nuclear Agency and the Defense Special Weapons Agency, respectively. The Government has certain rights in this invention.

BACKGROUND OF THE INVENTION

1. Field of the Invention

The present invention relates to vapor collection for trace constituent analysis, and more particularly, to vapor sampling by means of adsorbent polymers in which gases or liquids containing vapors are passed through beds of particles of adsorbent materials for further desorption of the vapor constituents into a flow stream for subsequent analysis.

More particularly, the present invention is related to a valveless, low power, ambient temperature vapor sampling system in which an in-line "trap", i.e. sorbent tube, containing adsorbent material, mechanically opens directly to a surrounding gaseous or liquid media for sample introduction and then seals to a unit containing a gas chromatographic column for thermal desorption and vapor injection into an analyzing system.

2. Description of the Prior Art

Vapor sampling by means of adsorbent polymers is a standard method of vapor collection for trace constituents analysis. In this process, gases containing vapors are passed through beds of particles of adsorbent material. Common examples of adsorbent materials include: Tenax TA, graphitized carbon black, and XAD Amberlites. Since materials differ in the affinities and capacities for absorbing the vapors of different compounds, the choice of adsorbent is based upon the sampling requirements and the specific vapors sought for collection.

Once vapors are sampled and adsorbed onto the surface of the adsorbent materials, the vapors are typically relieved by heating the adsorbent in the presence of a gas stream flowing past the adsorbent. This reversal of the process is typically called "desorption".

For many sampling applications, adsorbents are packed into small tubes, typically about ¼" or less in diameter, which are commonly called "sorbent tubes" or "traps". Since the sampling process can dilute vapors from a large volume of air onto a small amount of adsorbent and then desorb these vapors into a much smaller volume for subsequent analysis, the process is an important means for concentrating dilute vapors prior to analysis. For this reason, the process is sometimes called preconcentration and the sorbent tube or portion of the apparatus containing the sorbent tube is often referred to as a preconcentrator. The aforementioned process is an important part of many methodologies for analyzing vapor constituents in air.

The same process is routinely also applied to the analysis of volatile chemicals which are trace contaminants in the water using "purge and trap" analysis. A liquid sample is stripped of volatile constituents by bubbling a large volume of a purge gas, such as helium, through the liquid sample which then passes through a sorbent tube. The gas flow effectively transfers the volatile constituents from the liquid to the adsorbent surface. Heating the liquid sample can improve the effectiveness of the purging process. Following this transfer, the sorbent tube is heated to desorb the vapors into a flow stream for subsequent analysis.

One of the most common methods for sampling of airborne contaminants with sorbent tubes is to use a small pump to draw air through the sorbent tube. Small battery operated pumps are one of the options available for this purpose. Following sampling, the sorbent tubes are then loaded into an apparatus called a "thermal desorber", one of which is manufactured by Dynatherm Analytical Instruments, Inc., Kenton, Pa. Each sorbent tube is manually loaded and secured in a flow path using large thumbwheels with fittings having ferrules which slip over the end of the sorbent tube and are gas tight after compression with the thumbwheels.

For automated approaches using sorbent tubes, a sorbent tube is typically "plumbed" into a flow path controlled by a valve for switching between flows to be sampled and flows to carry away thermally desorbed vapors.

This approach has been used in small gas chromatographs for sampling and preconcentrating air samples for analysis. Two examples of chromatographs which use this approach, are the MINICAMS instrument manufactured by CMS Field Products Group, OI Corporation, Birmingham, Ala., and the Microfast GC manufactured by Analytical Specialists, Inc., Baton Rouge, La.

The operation of the preconcentrator tube in the MINICAMS instrument is described in U.S. Pat. No. #5,014,541, while the operation of the preconcentrator in the Microfast GC is described in U.S. Pat. No. #5,611,846. In both instruments, air is sampled through a check valve and onto an adsorbent trap. Additional flow paths with valving are then used to reverse the flow during thermal desorption to carry vapors away from the trap and into flow paths leading to chemical analysis.

FIGS. 1A, 1B, and 2 show standard in-line adsorbent trap preconcentrator. As shown in FIG. 1A, in the sampling mode, a vacuum pump (sample pump) and associated valve are activated drawing air through the check valve and the trap. During sampling, the flow restrictor 1 prevents pressurized gas in the analyzer detector from being significantly drawn through the trap in competition with flow through the inlet check valve pathway. In the injection mode, shown in FIG. 1B, the carrier gas valve 2 is activated to allow pressurized gas to reverse the flow through the trap, the flow restrictor 1, and on to the analyzer-detector. The zone 200 illustrates the portion of the apparatus that must be typically heated to prevent adsorption losses of semi-volatile compounds in the sampling pathways.

In a typical gas chromatograph system (GC) using a preconcentrator, shown in FIG. 2, the entire sample path must be heated including the inlet, the check valve, the four port compression feeding manifold, the plumbing line to the trap housing, the line leading to the vent for baking the trap of excess chemical vapors and the line leading to the flow restrictor 1. Due to the fact that these components are bulky, the power consumption requirement for "stand-by instrument ready" conditions is extremely high. The conventional heated inlet design, even when miniaturized, requires a warm-up time of approximately 30 minutes at an average power of more than 30W resulting in an energy requirement of approximately 16W-hours, while the subsequent GC analysis may only require an additional approximately 1–5W-hr over a few minutes time span by using high efficiency column-heating technology. Further difficulties experienced with standard preconcentrators as well as typical GC configurations using such preconcentrators, include:

1. The check valves typically have temperature limitations of approximately 200° C., which limits the temperature range of the sampling line. This temperature criteria limits the sampling of semi-volatile compounds: i.e., compounds having ambient temperature vapor pressures of approximately 1 mm or less, as these compounds condense on the walls of the sampling paths if they are not sufficiently heated.

The check valve is also susceptible to particulate contamination which may cause valve failure since the valve leaks when not seated properly.

2. The sampling lines and sampling inlet to the instrument also need to be heated sufficiently in order to pass lower volatility compounds of analytical interest. To avoid condensation losses ("wall losses") with these compounds, the plumbing may require significant heating unless the flow paths including valves have a very large flow capacity.

In the '846 U.S. Patent discussed above, temperatures on the order of 200° C. are typically required for the sampling of semi-volatile hydrocarbons. Heating these lines requires substantial power which may be a burden for small, battery operated instruments. A warm-up time for heating these lines can substantially increase the power burden to a small instrument by lengthening the time required for conducting a single or intermittent analysis. For example, a relatively large amount of power can be consumed through a 30-minute warm-up for an analysis only requiring 30–90 seconds of chromatography. Further, this approach results in continuously exposing heated surfaces at the inlet of an instrument which may also present fire and explosion safety concerns in industrial or hazardous environments.

3. The trap may be awkward to access, service and replace if it is integrated into the plumbing of the instrument. For example, if the trap becomes contaminated through excessive exposure to a difficult to desorb compound, it may be preferable to replace the trap rather than extensively bake the trap in an effort to slowly desorb the contamination. Additionally, the flexibility of introducing traps (or sorbent tubes) containing vapor samples to the instrument that exists with manual thermal desorbers is lost when they are plumbed in a somewhat more permanent plumbing arrangement.

Another disadvantage of the plumbed-in trap is that if the trap should mechanically fail for any reason (for example, one of the trap bed retainers has failed to contain the bed of adsorbent material in the trap), poor access to the trap can delay correct assessment of the instrument's performance problem.

4. Sample introduction with an in-line plumbedin trap is typically limited to gaseous samples while many samples of analytical interest are in liquid form. Liquid samples are not easily introduced quantitatively through the hot inlet and plumbing line and may contaminate the check valve and plumbing lines, as well as generate excessive solvent vapor for the trap and injection process to properly function.

A new system for vapor constituent analysis spare of disadvantages of the prior art systems is, therefore, desired for monitoring, sampling, and detecting trace compounds in the atmosphere, water, and other gases and liquids.

SUMMARY OF THE INVENTION

It is therefore an object of the present invention to provide a system for vapor constituent analysis having a valveless design, thereby avoiding temperature limitations and possible leakage associated with check valves.

It is another object of the present invention to provide a low power, ambient temperature system for vapor constituent analysis.

It is still a further object of the present invention, to provide a system for vapor constituent analysis having the advantages of an in-line permanent arrangement in combination with flexibility of manual thermal desorbers wherein the sorbent tube is simple to install, repair, and/or replace.

It is a still further object of the present invention to provide a system for vapor constituents analysis for both gaseous and liquid media of analytical interest.

In accordance with the present invention, a system for vapor constituents analysis of a media (gaseous or liquid) includes a gas chromatographic (GC) column connected by one end thereof to an analyzer-detector and an in-line preconcentrator assembly connected to the GC column at another end thereof. The system provides a sampling mode of operation, desorption mode of operation, and injection mode of operation.

Preferably, the preconcentrator assembly includes a trap housing identifying a media receiving compartment formed internally therein. Further included is a sorbent tube removably received within the media receiving compartment, and a transfer line unit coupled to the trap housing. The transfer line unit is directly connected to the gas chromatographic column at the end opposing the analyzer-detector.

It is important that the carrier means repositions the trap housing with respect to the transfer line unit so that it displaces the trap housing from the transfer line unit during the sampling mode of operation and couples (or seals) the trap housing to the transfer line unit during the injection mode of operation.

During the sampling mode of operation, a direct fluid communication path through an opening formed between the trap housing and the transfer line unit is established between the media receiving compartment within the trap housing and the surrounding media.

A sample pump is activated during the sampling mode of operation of the preconcentrator assembly to facilitate introducing of the surrounding media into the media receiving compartment. During the injection mode of operation, fluid communication is established between the media receiving compartment within the trap housing and the gas chromatographic column through the transfer line unit.

Usually, the adsorbent material contained within the sorbent tube is heated during the injection mode of operation in the presence of a carrier gas stream flowing past the adsorbent material. A carrier gas supply is activated during the injection mode of operation and provides a flow of the carrier gas through the media receiving compartment towards the gas chromatographic column simultaneously with the desorbing of the vapor constituents from the sorbent tube into the flow of the carrier gas. The released constituents are carried by the carrier gas to the gas chromatographic column for further analysis.

The trap housing preferably includes a trap body member and a trap end member threadingly and removably engaging the trap body member. An axial channel extends longitudinally through the trap body member and the trap end member throughout the entire length. A heater wire is wound around the sorbent tube within the axial channel along the part or portion extending along the trap body member. A heater wire support tube extends coaxially with the sorbent tube and is disposed between the sorbent tube and the heater wire. A system of sealing O-rings is mounted between walls of the trap housing and the sorbent tube. Preferably, the proximal end of the trap body member has a conical shape for facing the transfer line unit.

The transfer line unit includes a cylindrical body provided with a longitudinal channel and having a front end facing a conical proximal end of the trap body member. Preferably, a cylindrical recess is formed in the front end of the cylindrical body of the transfer line unit. In this manner, the conically shaped proximal end of the trap body member is received within the cylindrical recess. A capillary transfer line extends along the longitudinal channel of the transfer line unit and is maintained in place by a sealing O-ring. The capillary transfer line is heated by a heater wire wound around the capillary transfer line within the transfer line unit.

The present invention also provides a method of analysis of a medium for vapor constituents which includes the steps of:

provoding a preconcentrator assembly including a trap housing and a transfer line unit movable with respect to each other by carrier means, displacing the trap housing from the transfer line unit, positioning a sorbent tube into the media receiving compartment within the trap housing, activating the sampling pump thereby establishing a directed flow of a media surrounding the trap housing into the media receiving compartment therein, moving the trap housing by means of the carrier means towards the transfer line unit and providing air tight engagement therebetween, activating the carrier gas supply, thereby establishing a stream of the carrier gas flowing past the sorbent tube towards the gas chromatographic column, heating the sorbent tube, thereby releasing the vapor constituents into the carrier gas stream, and heating the transfer line unit.

It is important that the trap housing can reciprocate with respect to the transfer line unit and is capable of moving along an arc-like trajectory.

In one operating system concept, the sorbent tube and the gas chromatographic column are ramp heated during the desorption mode of operation while the transfer line unit is maintained at a required isothermal temperature.

These and other novel features and advantages of this invention will be fully understood from the following detailed description and the accompanying Drawings.

BRIEF DESCRIPTION OF THE DRAWINGS

FIGS. 7 and 8 show schematically another implementation of the trap housing and transfer line unit of the present invention;

DETAILED DESCRIPTION OF THE PREFERRED EMBODIMENTS

Figure 1A:
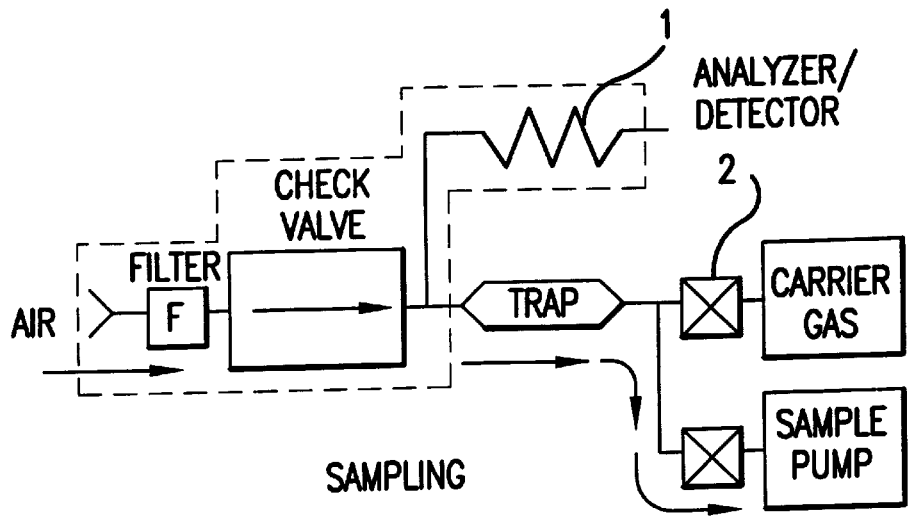
FIGS. 1A and 1B are schematic representations of the system using a preconcentrator of the prior art.
Figure 1B:
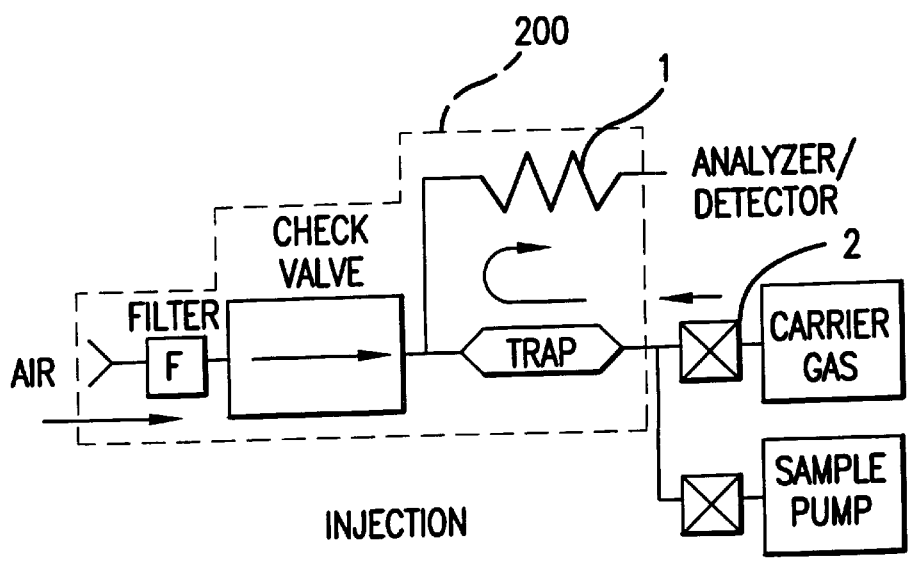
Figure 2:
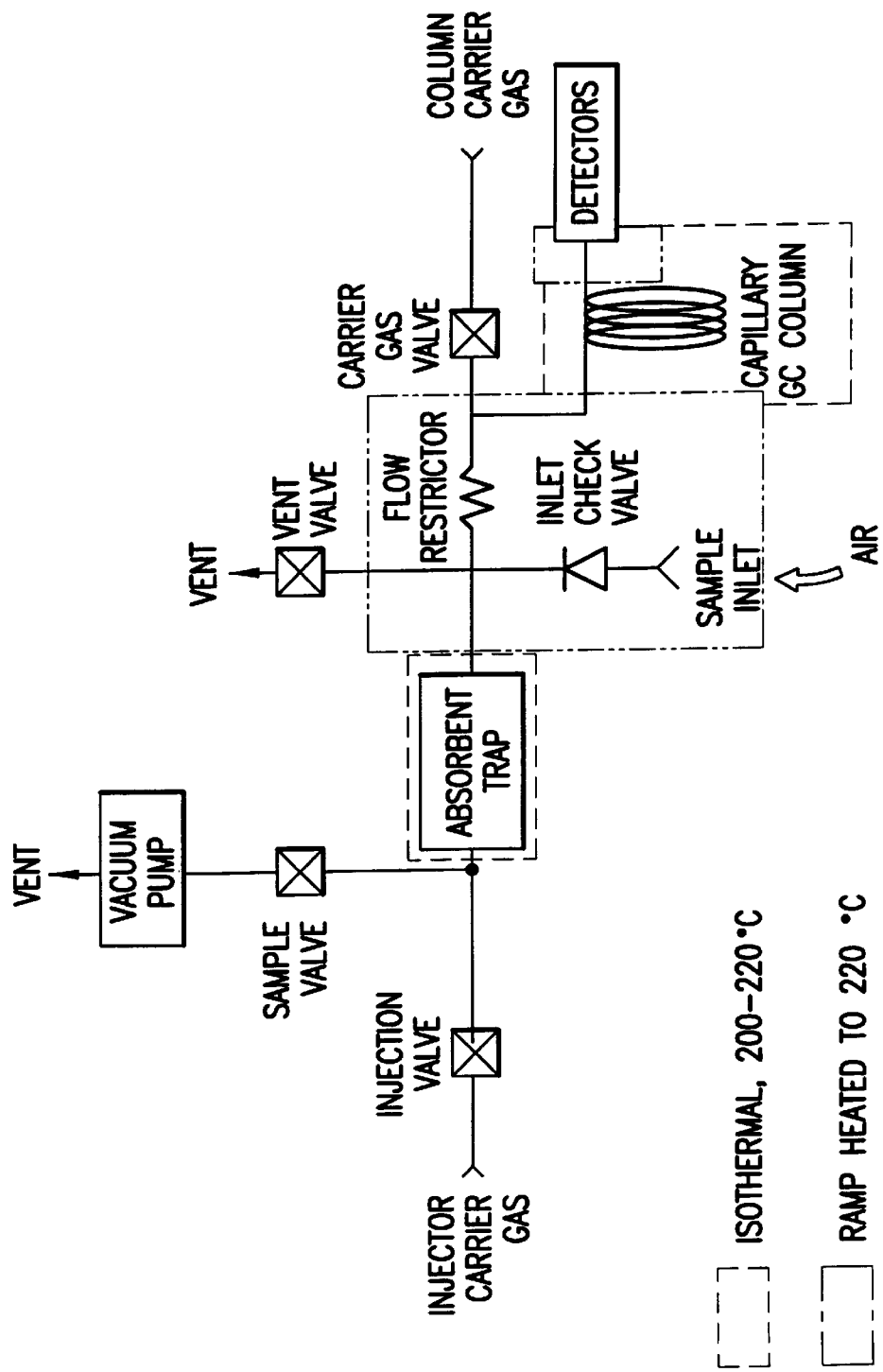
FIG. 2 is a schematic representation of the gas chromatographic system having an in-line preconcentrator of the prior art.
Figure 3A:
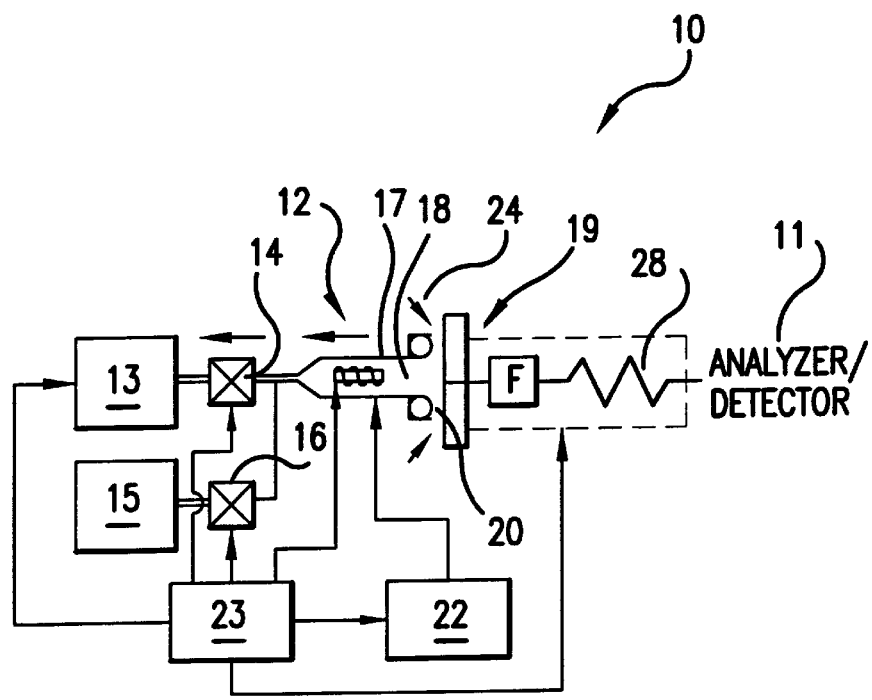
FIGS. 3A and 3B show schematically a system using an in-line preconcentrator of the present invention.
Figure 3B:
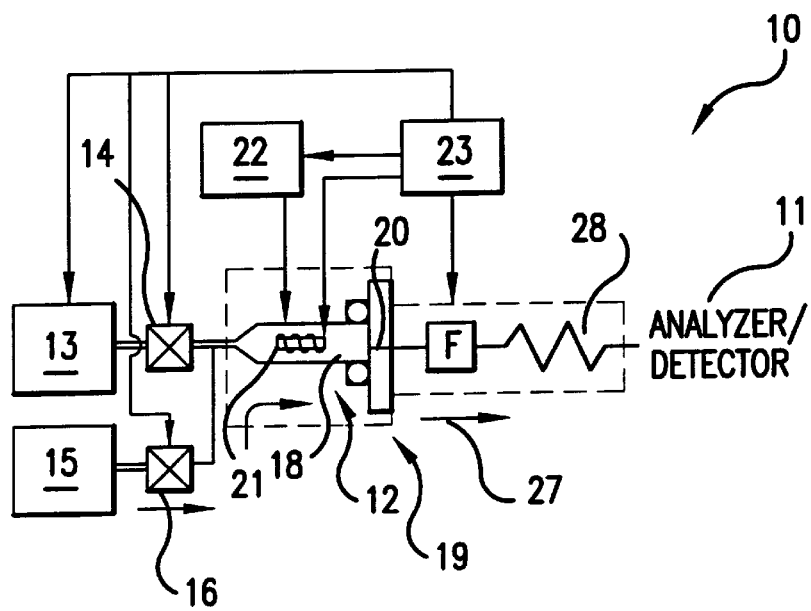
Figure 4:
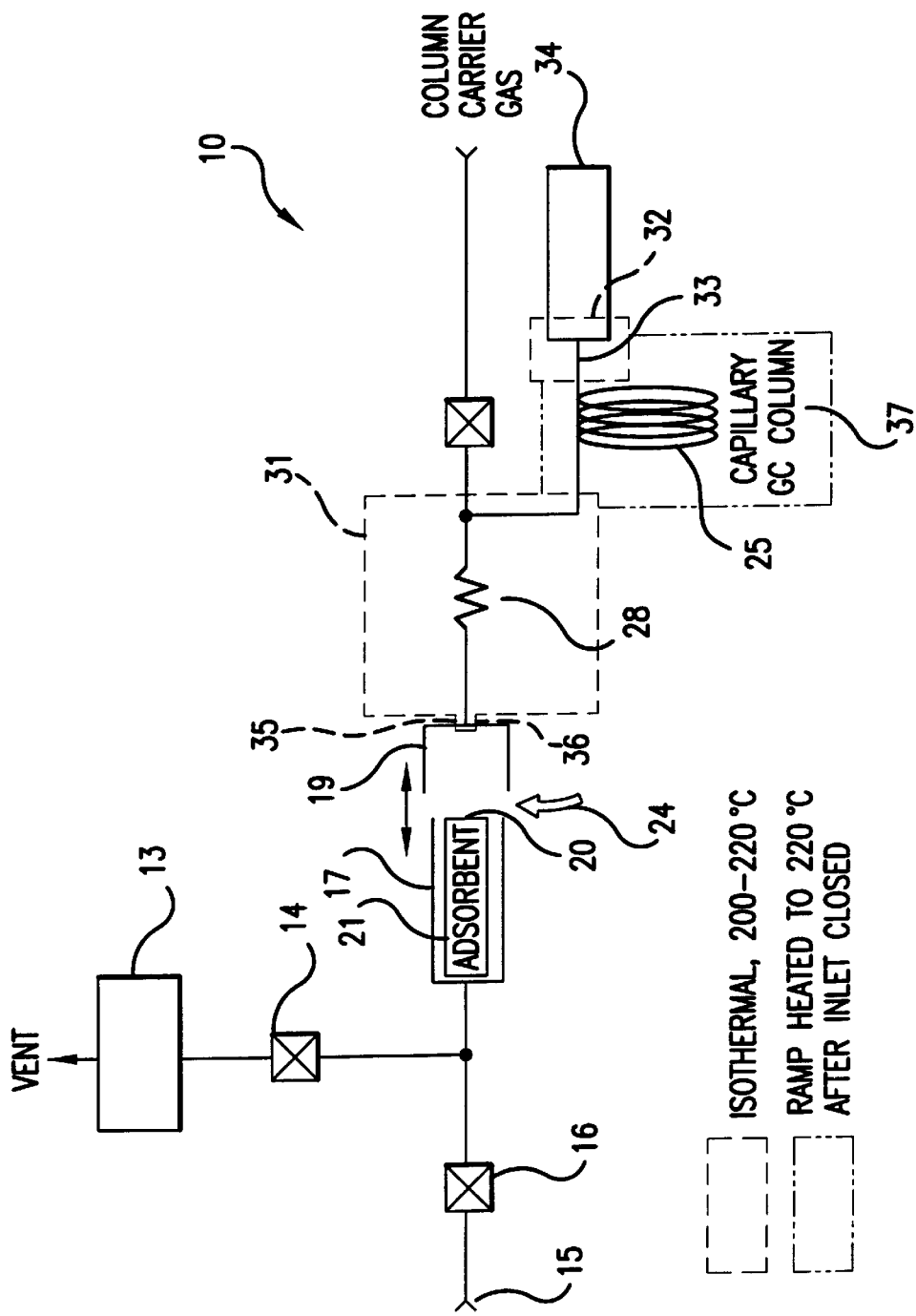
FIG. 4 is a schematic representation of a gas chromatographic system of the present invention.

Referring to FIGS. 3A, 3B, and 4, a system 10 for vapor constituent analysis includes an analyzing/detecting unit 11, an in-line preconcentrator assembly 12, a sample pump 13 with a sample valve 14, and a carrier gas reservoir 15 with an injection valve 16.

The preconcentrator assembly 12 includes a trap housing 17 having a media receiving compartment 18 formed within the trap housing 17, a transfer line unit 19 which is couplable to the trap housing 17 at the end 20. An adsorbent material 21 is removably received within the media receiving compartment 18 of the trap housing 17.

The trap housing 17 is moved with respect to the transfer line unit 19 by a carrier mechanism 22 (to be discussed in further paragraphs), which is controlled by a control mechanism 23. The control mechanism 23 (which is a computer interface with associated software) also controls the sample pump 13, sample valve 14, and the injection valve 16 to provide conformity between their operations and the mode of operation of the preconcentrator assembly.

The preconcentrator assembly 12 has three modes of operation: (1) a sampling mode, best shown in FIG. 3A, (2) an injection mode, best shown in FIG. 3B, and, (3) a desorbing mode of operation succeeding the sampling mode of operation and coinciding in time with the injection mode of operation.

During the sampling mode of operation, the preconcentrator assembly 12 is opened to the media 24 (which can be gaseous or liquid) surrounding the preconcentrator assembly 12. The trap housing 17 is displaced from the transfer line unit 19, as best shown in FIGS. 3A and 4 in order to allow a direct fluid communication path through an opening (or inlet) formed between the end 20 of the trap housing 17 and the transfer line unit 19. Open communication is established between the media receiving compartment 18 and the media 24 surrounding the preconcentrator assembly 12.

In the injection mode of operation, the trap housing 17 is positioned in airtight engagement with the transfer line unit 19, in order that fluid communication is established between the media receiving compartment 18 within the trap housing 17 and the analyzing-detecting unit 11 and particularly with the gas chromatographic column 25, as best shown in FIG. 4.

In the desorbing mode of operation, the adsorbent material 21 within the media receiving compartment 18 is heated in order to release the vapor constituents adsorbed on the adsorbent material 21 during the sampling mode of operation of the preconcentrator assembly 12 and which are supplied to the gas chromatographic column 25 for further analysis.

The adsorbent material 21 may be one of a number of adsorbent polymers capable of vapor collection, and may include, but is not limited to, Tenax TA, graphitized carbon black, XAD and Amberlites. As will be readily appreciated by those skilled in the art, the choice of the adsorbent material is based upon the sampling requirements and the specific vapors sought for collection. The adsorbent material 21 is preferably packed into a sorbent tube 26, or trap, which generally is a small tube having a diameter of ¼" inch or less.

As shown in FIGS. 3A, 3B, and 4, during the sampling mode of operation, the end 20 of the trap housing 17 containing the sorbent tube 26 with the adsorbent material 21, opens to the outside media thereby allowing direct sampling of the media which may be the surrounding air. The media contacts the adsorbent material 21 when the sample pump 13 is actuated with the sample valve 14 being opened by the control means 23. When the trap housing 17 is closed, the sorbent tube 26 is heated, and the carrier gas valve is opened by the control means 23. The pressurized carrier gas flow 27, shown in FIG. 3B, carries vapors desorbed from the adsorbent material 21 through flow restrictor 28 within the transfer line unit 19 to the gas chromatographic column 25 for further analysis.

By making and locating the sorbent tube 26 and its heating component (to be described in further paragraphs) internal to the trap housing 17, the components are completely shielded from the surrounding air. During the sampling mode of operation, all the exposed preconcentrator assembly components are unheated. This significantly reduces power and safety concerns regarding environmental exposure of heated components.

Since the trap housing 17 is openable, the sorbent tube 26 contained therewithin can be directly accessed. This allows for easy removal and exchange of sorbent tubes. For example, sorbent tubes may be sampled elsewhere and introduced to the preconcentrator assembly 12 for desorption and further analysis. Similarly, if a sorbent tube appears contaminated with chemicals and is found difficult to clean, it may be easily exchanged for another.

Figure 3C:
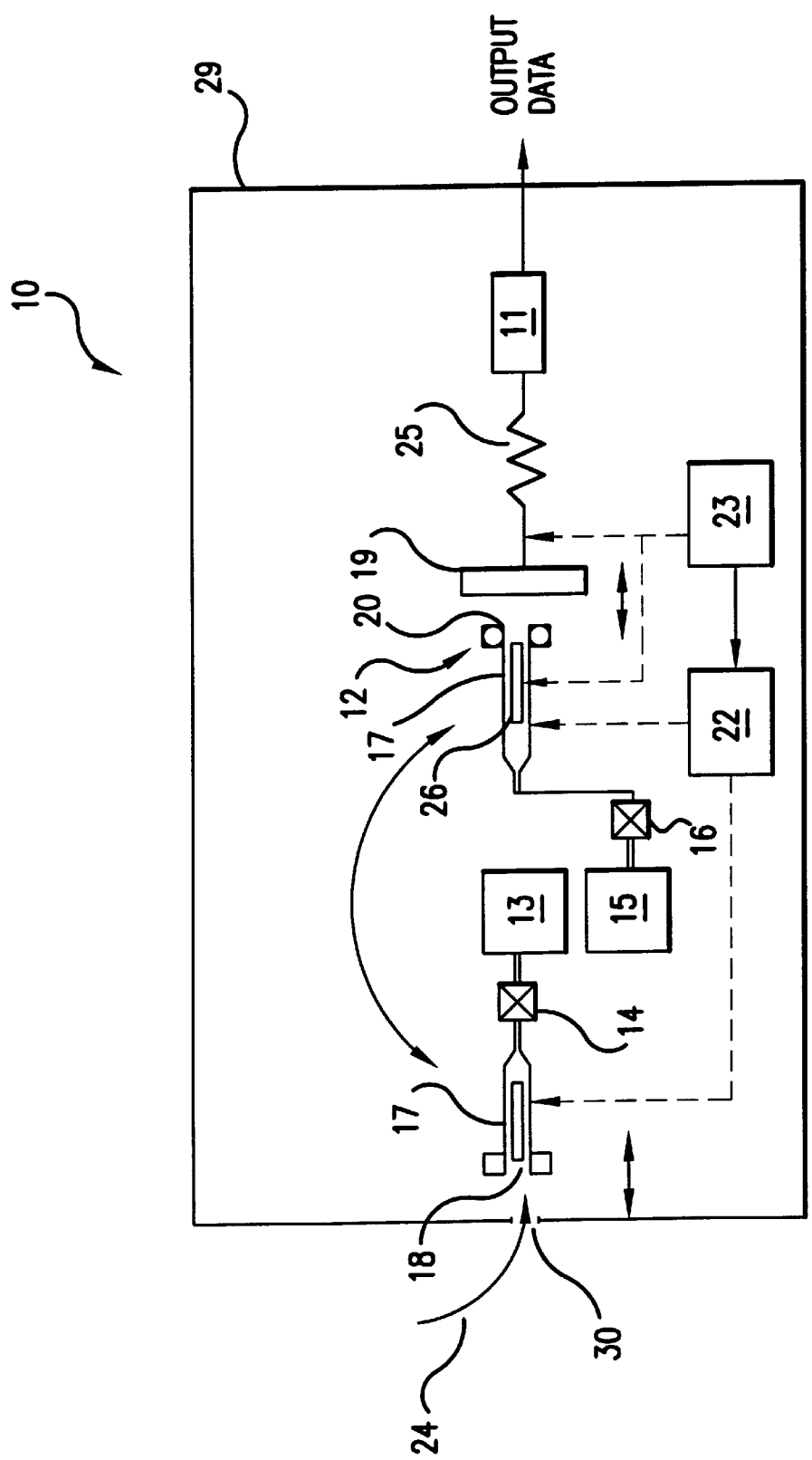
FIG. 3C shows somewhat schematically an alternative embodiment of the system of the present invention.

Additionally, the structure of the preconcentrator assembly 12 allows for additional degrees of motion to be added, so that other connections may be formed and broken, as shown in FIG. 3C. For example, the trap housing 17 can be displaced from the transfer line unit 19 by traveling approximately 50% of the available travel on a linear slide (to be discussed further), rotated 180° and then travel the remaining 50% distance available on the slide.

In this approach, the trap housing 17 may be sealed to an alternate seat for sampling a special flow path or desorbing by an alternate analyzing-detecting unit. This approach can be used, as shown in FIG. 3C for example, to flip the trap housing 17 around within the housing 29 of the entire analyzing instrument and allow the trap housing travel to meet an opening 30 in the instrument housing 29 for introducing a sample into the media receiving compartment 18 within the trap housing 17. After sample introduction, the trap housing 17 retracts from the opening 30 in the housing 29, rotates and then seats with the transfer line unit 19 leading to the gas chromatographic column 25.

The open-closed arrangement of the preconcentrator assembly 12, also allows for the introduction of a liquid sample directly to special tubes containing an inert packing, such as glass wool. If desired, the trap tube while opened to the air, may be heated to evaporate the solvent without desorbing the less volatile compound. This may greatly reduce detector interference caused by injecting large amounts of solvent vapor.

The complete gas chromatographic system shown in FIG. 4 is capable of sampling and analyzing volatile and semi-volatile compounds. The flow restrictor 28 is a relatively small piece of tubing which requires little power to maintain a constant temperature in the range of 200–220° C.

The flow restrictor zone 31 and zone 32 between the end 33 of the gas chromatographic column 25 and detectors 34 can be combined into one compartment and jointly maintained at the required isothermal temperature. Alternatively, the zones 31 and 32 may be "flash heated" during the analysis of a sample. The column 37 and adsorbent 21 are dynamically heated and draw power only briefly while the particular component of the system is active in the instrument.

The sorbent tube 26 is heated during thermal desorption. The sorbent tube 26 is generally small and has a low thermal mass to reduce power during thermal desorption. The zone 35, containing the transfer line 36 and connecting the transfer line unit 19 of the preconcentrator assembly 12 to the isothermal heated zone 31 (containing the flow restrictor 28 and the plumbing connections to the gas chromatographic column 25 and the detectors 34), is "flash heated" during thermal desorption of the adsorbent material 21. This approach also reduces power consumption since this transfer line 36 needs only to be heated during sample introduction to the gas chromatographic column 25.

The capillary gas chromatographic column zone also is subject to a temperature programmed rather than isothermal gas chromatography. Using "flash heated" components with the system of the present invention, there is no warm-up power required for the operation of the instrument and the only power needed is approximately 1–5W-hr required for the gas chromatography analysis using high efficiency heating, including the "flash heated" operation of the preconcentrator assembly 12.

Figure 5:
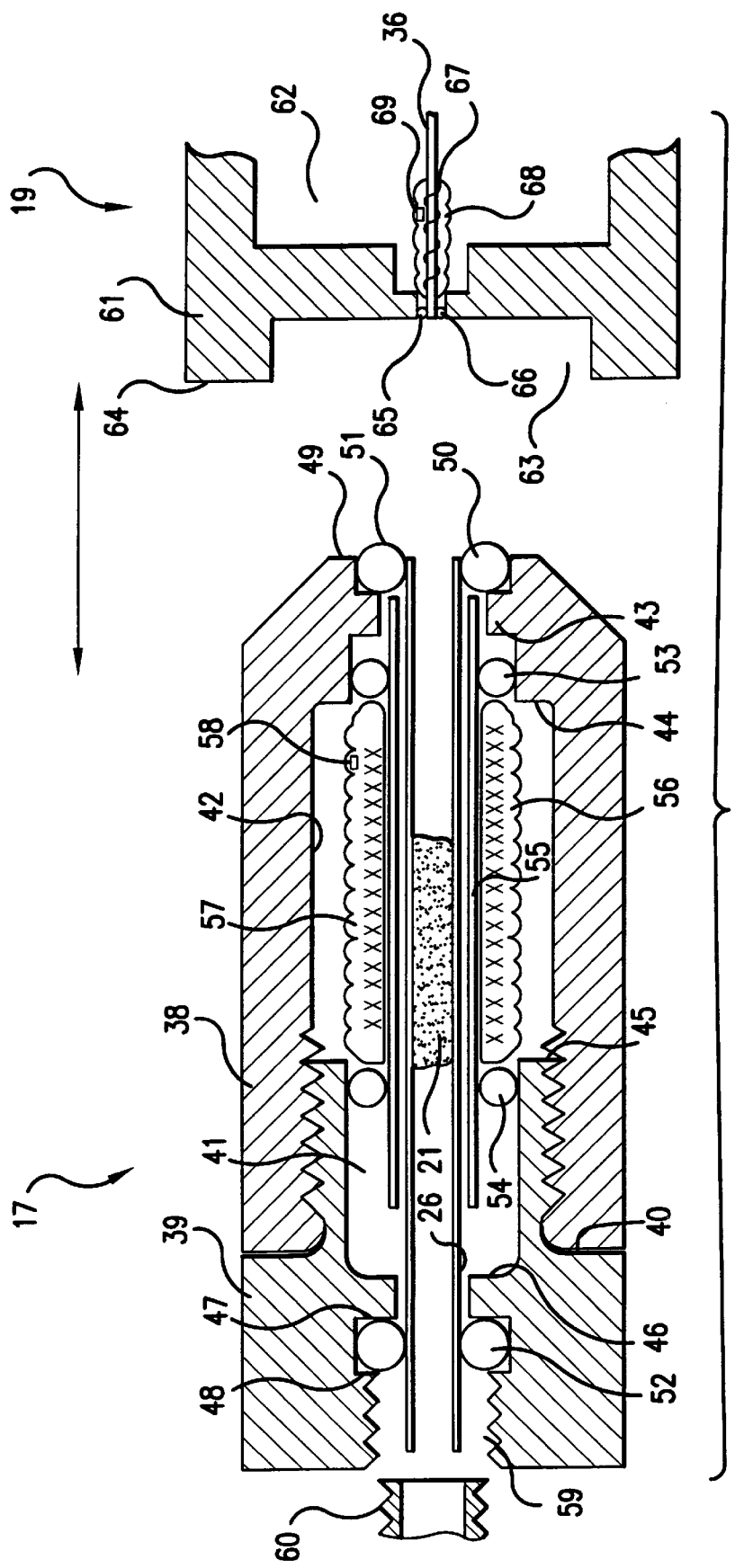
FIG. 5 shows a longitudinal cross-section of the trap housing and transfer line unit of the preconcentrator assembly of the present invention.
Figure 6:
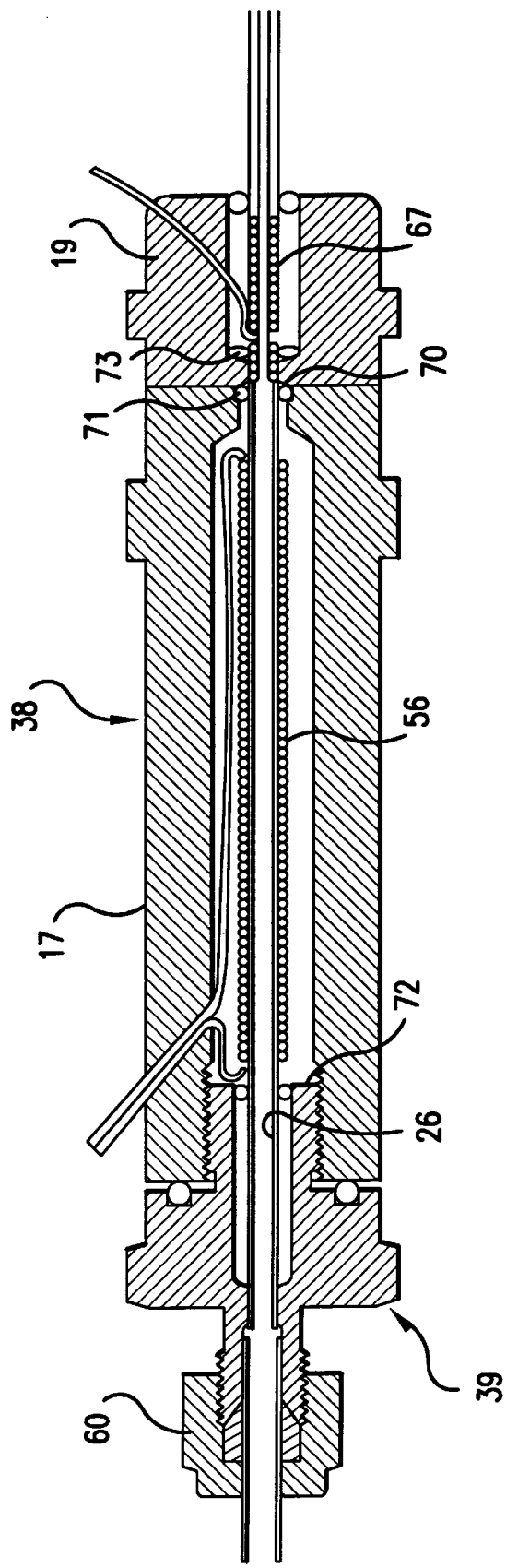
FIG. 6 is a longitudinal cross-section of the trap housing coupled to the transfer line unit of the alternative embodiment of the preconcentrator assembly of the present invention.

Several designs of the trap housing 17 and transfer line unit 19 shown in FIGS. 5–6 have been made and tested. As shown, the trap housing includes a trap body member 38 and a trap end member 39 threadingly engaging the trap body member 38 at the distal end 40 thereof. An axial channel 41 extends longitudinally through the trap body member 38 and the trap end member 39.

The internal walls 42 of the axial channel 41 (both at the trap body member part and the trap end member part) are provided with multiple flanges 43–48 which change the cross-sectional profile of the axial channel 41 along the length thereof for better temperature distribution. This has the added function of maintaining the sealing O-rings in fixed position. At the proximal end 49, the trap body member 38 is provided with a shallow bore 50 in which a front O-ring 51 is seated. A back O-ring 52 is placed within the axial channel 41 between the flanges 47 and 48 which maintain the back O-ring 52 in place.

In addition to the front and the back O-rings 51 and 52, O-rings 53 and 54 are mounted inside the axial channel 41 and position the heater support tube 55. Sorbent tube 26 fits into the axial channel 41 (which constitutes the media receiving compartment 18) through the front and back O-rings 51, 52 which aids in forcing air flow through the sorbent tube 26. The front O-ring 51 forms a face seal with the transfer line unit 19.

A heater wire support tube 55 extends coaxially with the sorbent tube 26 along the portion of the sorbent tube fitted in the trap body member 38. Both glass and brass support tubes may be used, however, brass is preferred since brass conducts and transfers heat faster than glass. Obviously, brass has the added advantage of being less fragile than glass. A heater wire 56 is wound around the support tube 55 substantially between the flanges 44 and 45 within the axial channel 41. A ceramic fiber insulation 57 is provided within the axial channel 41 for insulation of the brass tube 55 from the heater wire 56.

An RTD or thermocouple sensor 58 is placed with the insulation 57, either between the brass tube 55 and the heater wire 56, or outside the heater wire 56. The inside position of the sensor 58 is preferable to allow for a more accurate reading of the inner temperature during the desorption mode of operation. The O-rings 53 and 54 are positioned between the internal walls 42 of the axial channel 41 and the brass support tube 55 to further prevent leakage and to optimize heat distribution within the axial channel 41.

The trap end member 39 has a threaded bore 59 which receives connections 60 of the sample pump 13 and the carrier gas reservoir 15, as best shown in FIGS. 5–8. Any other connections known to those skilled in the art are also contemplated in the scope of the present invention with the main requirement being that the connections provide a pressure tight seal between the axial channel 41 and the outside of the instrument.

The transfer line unit 19, as shown in FIG. 5, includes a cylindrical body 61 having a longitudinal channel 62. The cylindrical body 61 is provided with a cylindrical recess 63 formed at the face end 64 of the cylindrical body 61. An opening 65 is formed centrally of the cylindrical recess 63 allowing the transfer line 36 (extending within the longitudinal channel 62) to protrude through the opening 65.

The transfer line 36 is formed of glass lined steel capillary tubing which seats in the transfer line unit 19 with an O-ring 66 holding the transfer line 36 within the opening 65 and forming a small dead volume interface inside the face seal of the front O-ring 51 on the trap housing 17, and the face of the cylindrical body 61 of the transfer line unit 19.

The small O-ring 66 eliminates the need for the glues to position the transfer line in the cylindrical body 61 and permits the transfer line unit 19 to be exchanged easily when needed. The small O-ring 66 also allows the heater wire 67 wound around the transfer line 36 extends to an end thereof, while being separated from the transfer line unit 19 by an air space. This greatly reduces heat conduction and provides more complete heating of the metal transfer line 36 near the face end 64 of the cylindrical body 61. The use of metal for the metal capillary transfer line also helps with heat distribution near the face end 64.

As shown in FIG. 5, the trap body member 38 has a bevel on the proximal end 49 of the trap body member 38 to help align the proximal end 49 with the transfer line unit 19 by its alignment with the cylindrical recess 63 made in the face end 64 of the cylindrical body 61.

A small amount of mechanical play is deliberately built into the fasteners which attach the trap housing to the carrier mechanism 22 (discussed in further paragraphs) in order that it has sufficient freedom to self-align in a high precision manner with the transfer line unit 19. Although not shown, it is also contemplated in the scope of the present invention to have the cylindrical trap housing 17 lying in the rectangular milled slot of the carrier mechanism held within the slot by a spring loaded screw. By adjusting the tension of the spring, it is possible to vary how firmly the trap housing 17 is held in the carrier mechanism.

Similar to the trap housing 17, a ceramic fiber insulation 68 and RTD or thermocouple sensor 69 are also provided in the cylindrical body 61 of the transfer line unit 19.

An alternative design is shown in FIG. 6, wherein a dead volume between the sorbent tube 26 and the transfer line 36 is minimized through a face seal in which a small lip 70 is pressed against an O-ring 71 seated at the end of the trap housing 17.

O-rings 71 and 72 at both ends of the sorbent tube 26 force air flow through the sorbent tube 26. In this design, epoxy glue 73 was used to secure the end of the glass capillary transfer line 36 and its heater wires 67 to minimize dead volume and to prevent leakage.

The design shown in FIG. 5 has some advantages over the design of FIG. 6, since the glass capillary transfer line 36 may be subject to breakage and it is not replaceable because of the epoxy glue 73.

Another embodiment of the trap housing 17 and the transfer line unit 19 is shown in FIGS. 7 and 8. According to this implementation, a stem 74 fits through a large O-ring 75 in the trap body member 76 to form a pressure tight seal. The sample pump 13 and the carrier gas reservoir 15 connections are made to the plastic tubing 77. Inside the stem 74, a small glass sorbent tube 26 containing Tenax packed with glass wool plugs 78 is introduced through a small O-ring 79 in the nose 80 of the stem 74 forcing the carrier gas to flow through the sorbent tube 26 during desorption. Fine heater wire 81 is wound around a thin walled glass tube 82 which is a structural support for the heater wire 81. In the transfer line unit 19, a glass capillary tube 83 is wrapped with wire 84, sleeved with Teflon tubing 85 and glued closed at an end with epoxy glue 86. The tube 83 is seated in a ferrule to force carrier gas flow during the injection mode of operation in the only available path, i.e., the "flash heated" capillary transfer line to the gas chromatographic column. Although having certain shortcomings in comparison with the preferred embodiment shown in FIG. 5, such as unwanted dead volume 87 (seen in FIG. 8), this design clearly demonstrates in detail the functioning configuration of the invention.

All three designs shown in FIGS. 5–8, demonstrated a very low leak rate of pressure and negligible temperature rise on the outside surface when heating of the assembly for 30 seconds to 230° C. Helium leak rates of less than 0.1 ml/min were measured with carrier gas pressures in the range of 20–30 psi.

A number of different mechanisms have been developed and tested for opening and closing the preconcentrator assembly 12 of the present invention. For reciprocating movement of the trap housing 17 with respect to the transfer line unit 19, linear slides have been developed with miniature roller bearing slides of lengths in the range of 2 or 3". To actuate the slides, lead-screw devices, pneumatic devices, threadless Rholix screw type devices, and rack-and-pinion gear head-driven devices may be used for the preconcentration assembly 12. Basically, any mechanism which can control linear motion is contemplated in the scope of the present invention. To maintain a seal under carrier gas pressure during desorption and sample injection through the transfer line interface, it is necessary to maintain the application of pressure to the interface between the proximal end of the trap housing 17 and transfer line unit 19. For this reason, the use of lead-screw type devices have been contemplated in the scope of the present invention.

Another closely related issue is the torque required to reverse and open the parts when desired. It has been found that DC motors which drive an O-ring compression seal to a certain torque before they stall, often do not have sufficient torque when the same DC voltage is applied to the motor in the reverse direction to open the parts of the preconcentrator assembly. A number of experiments with limit switch motors capable of providing too much torque and compression of the O-ring face seal to stop the motors at the desired point have been conducted. It was difficult to fine tune the exact position of limit switch actuation and maintain these settings over periods of time. Strain gauges as mechanical linkages to the fittings were also tested that gave a graded response related to the pressure applied to the fittings. Two basic mechanisms have been found to work the best for the system of the present invention, which are:

(1) the use of clutches with lead screws, and, (2) miniature motors with lead screws driven to their stalling point under electronic control with multiple DC drive voltages. In the latter approach, a reduced voltage such as 18V can drive the motor to achieve a sufficient O-ring face seal with the preconcentrator, and a larger voltage such as 24V can be transiently applied in the reverse direction to achieve travel with the lead screw in the opposite direction. In combination with this multiple voltage control of the motor turning the lead screw, the lead screw attachment to the moving trap housing 17 is cushioned with a spring. The compression of this spring reduces the abruptness of the stop and O-ring compression when the moving part reaches the end of its travel.

In an alternate approach, clutches have been successfully used to limit the compression of the O-ring seal when the preconcentrator assembly 12 has reached the limit of their travel. In one approach, a Rohlix clutch has been used to control the linear motion and limit the compression at the end of the travel. The Rohlix clutch is a threadless lead screw system in which a smooth rod is turned by a motor. Surrounding the rod, is a set of canted bearings which trace a helical path on the rod as the rod is turned inside the bearings. If not allowed to freely turn with the rod, this helical path causes the housing with the bearings to travel along the rod. However, if the housing with the bearings meets an obstacle through its travel, then it will slip on the rod and remain in that position.

By adjusting how tightly the bearings grip the rod, the force required to make the bearings slip may be adjusted. In this approach, the Rohlix clutch provides linear translation by attaching the clutch to a linear slide. As with a lead screw, this motion is bi-directional according to the direction of the motor. By attaching the trap housing to the clutch, the trap housing travels with the clutch until it seals with the transfer line unit with a pressure determined by a setting of the clutch's slipping point. Perhaps because of small inherent amount of slip in the Rohlix clutch system, such a system does not require multiple voltages to reliably reverse and open a system.

Figure 9:
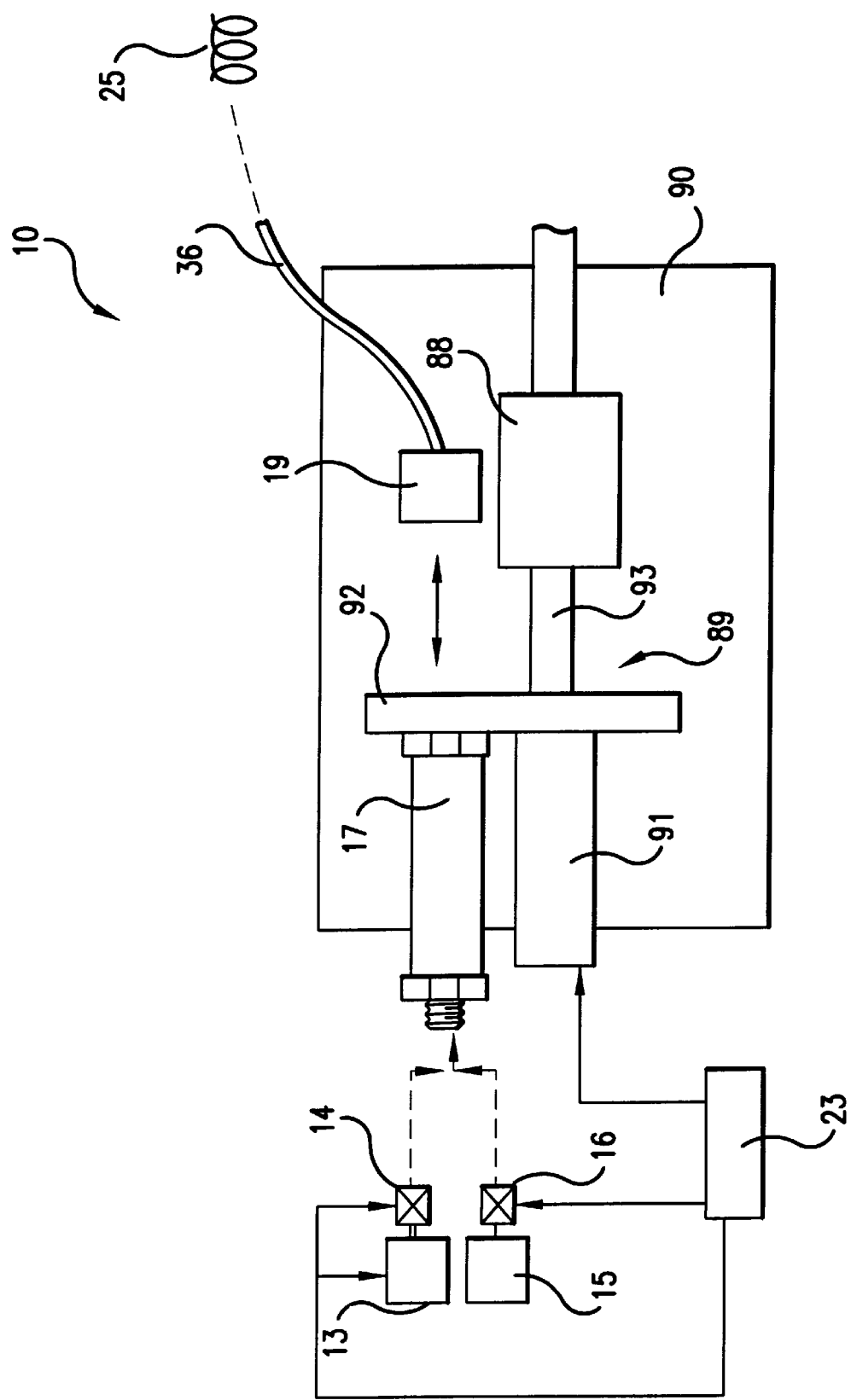
FIG. 9 shows schematically the preconcentrator assembly of the present invention using a Rohlix clutch as a carrier mechanism.
Figure 10:
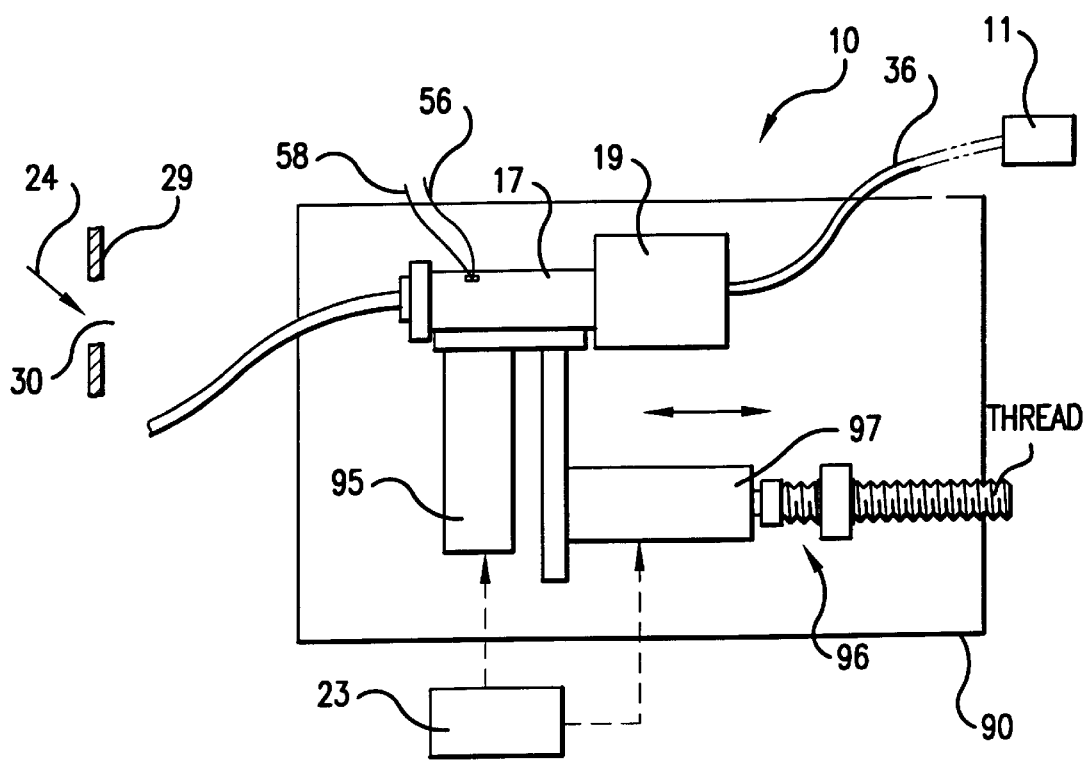
FIG. 10 shows schematically another implementation of the preconcentrator assembly of the present invention in which the trap housing is capable of both reciprocating and rotating with respect to the transfer line unit.

Shown in FIG. 9 is a preconcentrator assembly 12 using the Rohlix clutch 88. A small linear slide assembly 89 is mounted to the base plate 90 with the motor 91 and the trap housing 17 attached to the slide 92. The motor 91 with its gear reduction turn the smooth rod 93 which extends through the Rohlix clutch 88 secured to the base plate 90.

The Rohlix clutch has six canted bearings to convert the rotation of the smooth rod 93 into the linear translation of the assembly on the slide 89. The unit is integrated with the gas chromatography system by connecting valve carrier gas and the sample pump to the trap housing 17 and connecting the flash heated transfer line 36 to the gas chromatography column. In this example, electronic signals from a computer interface (control means) 23 provide either +12 volts or −12 volts to the motor 91 through a standard driver interface circuit to effect either the opening or the closing of the preconcentrator assembly 12.

The operation sequence is as follows:

1. Open the preconcentrator assembly 12 by means of the computer interface;

2. Turn on the sample pump 15 and pump valve 14 for sampling through the computer interface and valve driver interface;

3. Turn off the sample pump 13 and sample valve 14 after sampling sufficient media 24 into the media receiving compartment 18;

4. Close the preconcentrator assembly 12;

5. Activate a heater circuit through the computer interface to heat the trap housing to the desired temperature (e.g., 220° C.). In this particular example, a thermocouple was used to sense the temperature adjacent to the heater wire 56 around the sorbent tube 26 within the trap housing 17; feedback from the temperature sensor to the heater circuit controls the heating of the sorbent tube; this heating is usually done very quickly with helium present in the sorbent tube rather than air;

6. Turn on a heater wire 67 heating the transfer line 36 within the transfer line unit 19 (e.g., 250° C.) by means of the computer interface to ready it for sample transit;

7. Activate the carrier gas valve 16 which flows desorbed vapors through the heated transfer line 36 to the gas chromatographic column 25 by means of the computer interface;

8. Turn off, by means of the computer interface, the heater wires for the sorbent tube and the transfer line and turn off the flow of carrier gas through the preconcentrator assembly 12;

9. Finally, gas chromatography assembly (analyzing/detecting unit 11) carries out the analysis of the injected vapors.

An example analysis of a fast, low resolution operation of the hydrocarbons dodecane through hexadecane (adsorbent material) was performed using the perconcentrator assembly of the present invention. The gas chromatography analysis was accomplished with a temperature programming rate of 2° C. per second with three meters of a 0.25 mm I.D. DB-1 code fused silica capillary column.

Figure 11A:
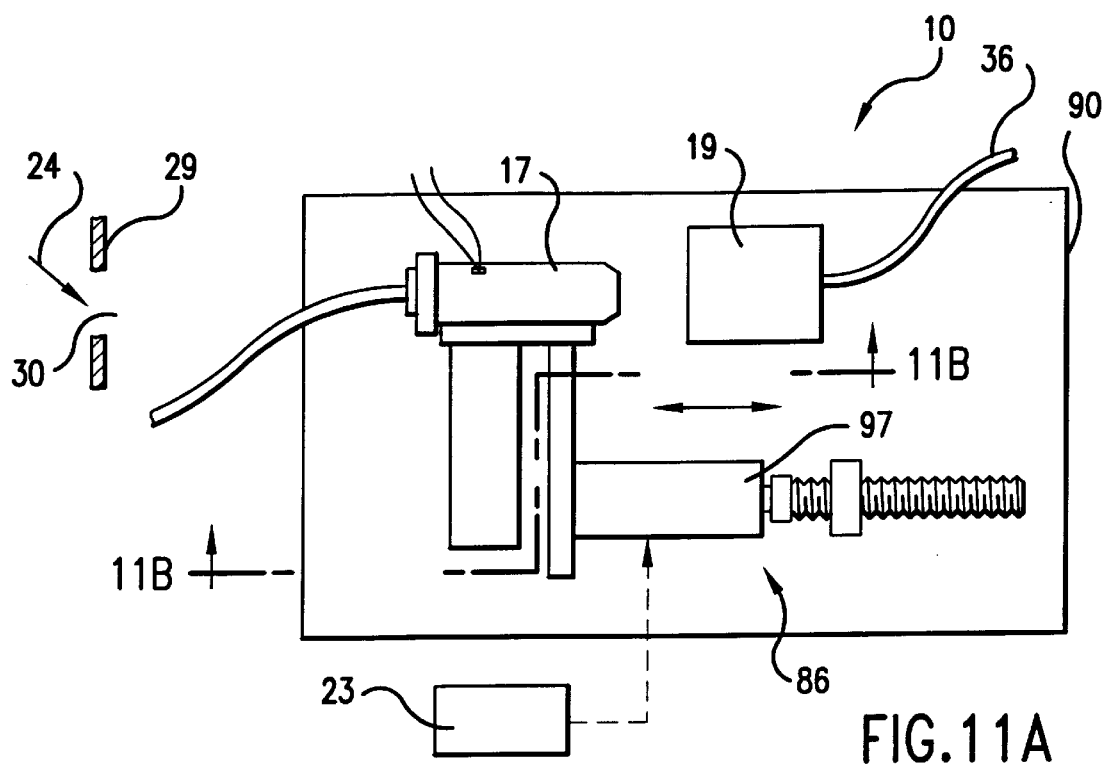
FIG. 11A shows schematically the preconcentrator assembly of FIG. 10 in an open position with the trap housing reciprocating with respect to the transfer line unit.
Figure 11B:
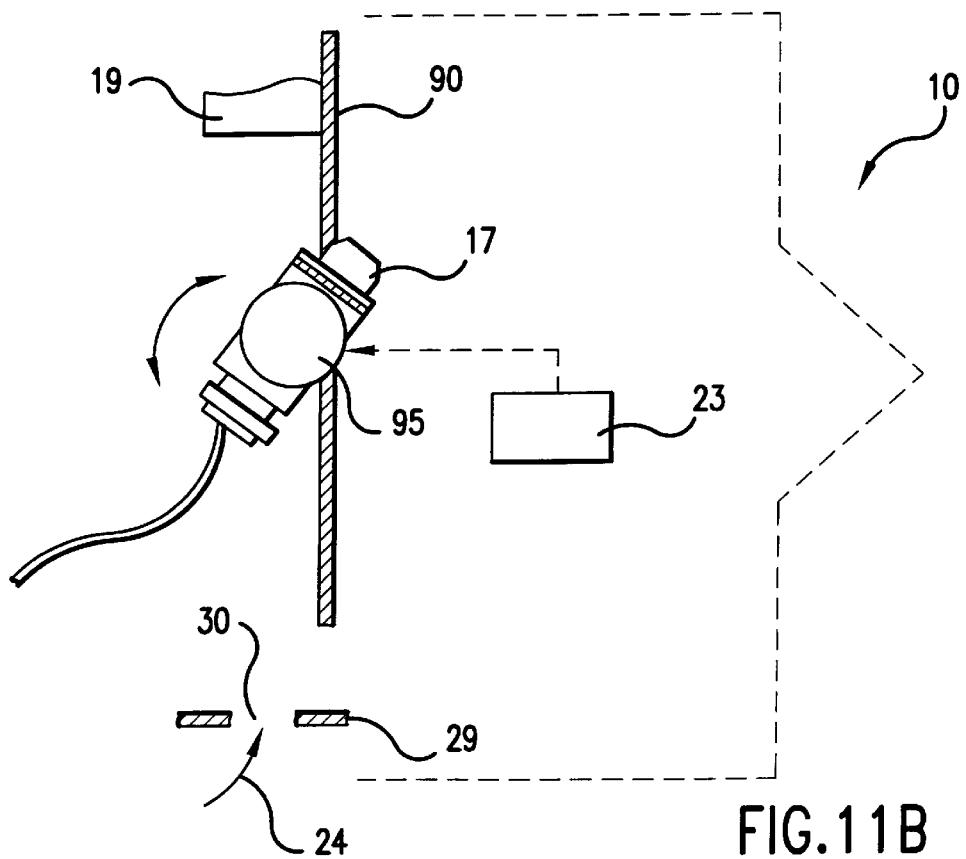
FIG. 11B is a view of the preconcentrator assembly of FIG. 11A taken along lines 11B—11B with the trap housing rotating.

A more advanced implementation of the preconcentrator assembly of the present invention is shown in FIGS. 3C, 10, 11A and 11B. To facilitate the preconcentrator's interface with both the sampling inlet (opening 30) in the housing 29 and the gas chromatography assembly (analyzing/detecting unit 11) within the instrument, the preconcentrator assembly 12 is provided with a second motor 95 which rotates the assembly 180° in addition to the motor 97 which slidably displaces the trap housing 17. Mechanical "stops" control the limits of rotation in this design, although many other approaches to rotation control are contemplated in the scope of the present invention, such as stepper motors, or like mechanisms. A simple valve, consisting of a rubber septum with slits in its center may be used in the sampling inlet 30. Such an inlet opens when pressed in the center from behind by the nose of the trap housing 17 when in position for sampling. The operation for this preconcentrator assembly is described as follows:

1. The computer interface 23 controls the motion of the trap housing 17 and moves it by means of the motor 97 to the sample inlet 30 where it pushes open the septum valve;

2. The sample pump 13 and sampling valve 14 are turned on to effect air sampling;

3. After a programmed duration of sampling, the sample pump 13 and the sampling valve 14 are turned off;

4. As shown in FIG. 11A, the computer interface 23 retracts the trap housing 17 from the inlet using the lead screw actuator 96 with the motor 97 to approximately the midpoint of the travel of the slide;

5. An electronic sensor is fabricated into the slide which provides a signal through a digital circuit when this point is reached to turn off the lead screw motor 97 (there are a variety of optical encoding methods and sensors which can be used to sense and control position which can be used for this purpose);

6. As shown in FIG. 11B, the computer interface 23 then operates the motor 95 which rotates the trap housing 180°;

7. The lead screw motor 97 is again actuated to continue the linear motion with sufficient time to the trap housing nose to seat with the transfer line unit 19 and stall the lead screw motor 97;

8. The transfer line and sorbent tube heater circuits are activated; both have temperature sensors and independent temperature set points that are computertrolled; controlled; the computer 23 uses programmable analog output voltages to set the target temperatures for the temperature controller circuits;

9. The carrier valve 16 is actuated to effect the injection of desorbed vapors through the transfer line into the gas chromatography 10. Following injection or gas chromatography analysis of the vapor sample, the trap housing 17 is backed to the point sensed by the opto-electronics sensor, rotated 180°, and translated forward to the sample inlet for collecting the next vapor sample.

The above-described approach in which the lead screw operates until the motor stalls at the travel limit allows a very small, low power motor to provide sufficient force to seat the mechanism. Since equal in magnitude, but opposite in sign, voltage may not be adequate to open or dislodge the lead screw mechanism, a brief pulse of higher DC voltage to the motor is applied to start the lead screw from a seated position. This two step voltage control of the actuator is accomplished by using analog electrical signals in combination with motor direction control circuits.

Figure 12:
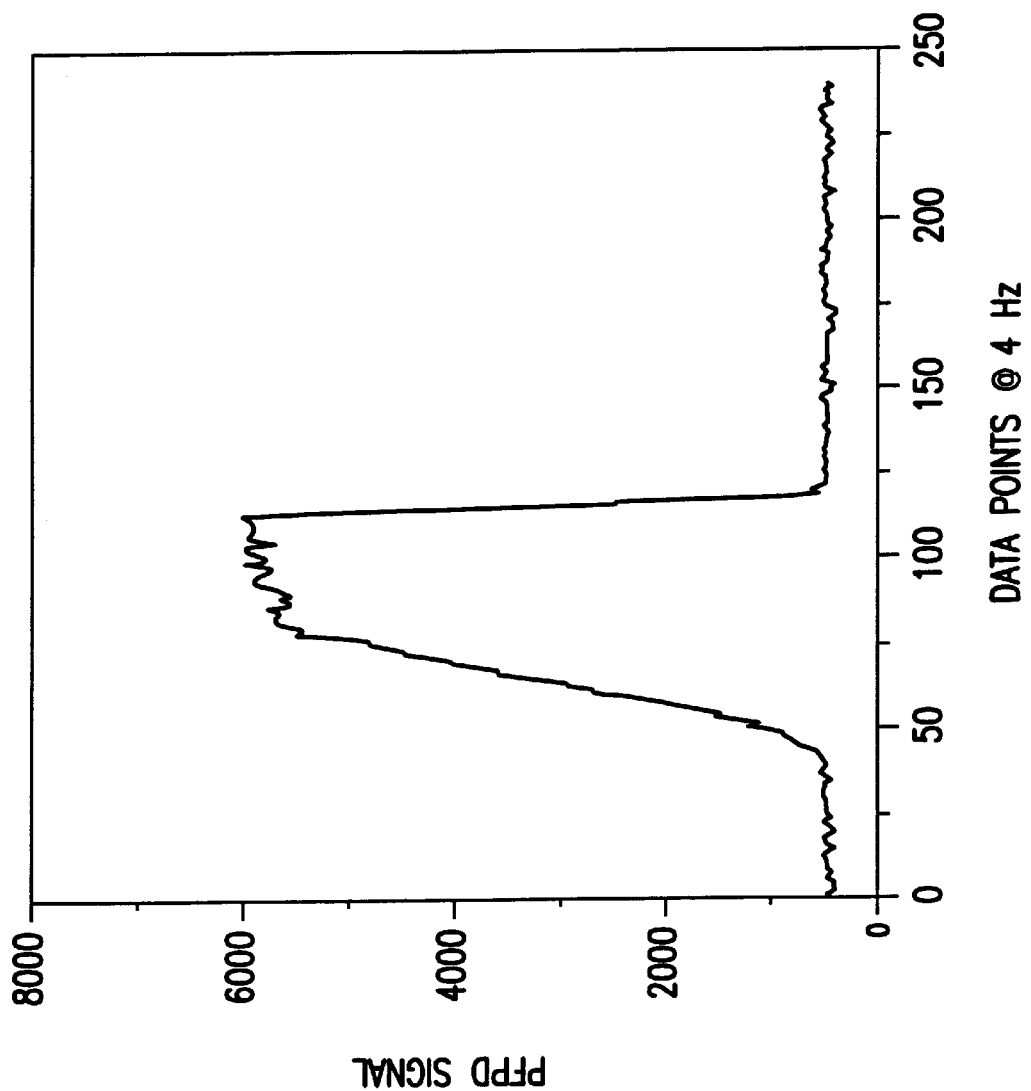
FIG. 12 is a diagram showing chromatographic data received with the preconcentrator assembly of the present invention for the sampling of trace concentrations of a light volatile compound in air.

An example of chromatographic data with the above system for the sampling of trace concentrations of a light volatile compound in air is shown in FIG. 12. Dimethyl sulfide at 500 parts per trillion (ppt) was sampled for 240 seconds using a sorbent tube containing 3 mg of Carboxen adsorbent (Supelco, Inc., Bellefonte, Pa.) with a flow rate of approximately 100 mL/min. A pulsed flame photometric detector (OI Corporation, Station College, Tex.) collected data at a rate of 4 Hz from the GC column which, because of the high volatility of dimethyl sulfide, was operated isothermally at 40° C. The slight retention of the compound on the 10 m×0.18 mm DB-1 GC column under these conditions results in a peak shape reflecting the time-dependent heating, desorption and injection flow timing of the compound from the trap.

Figure 13:
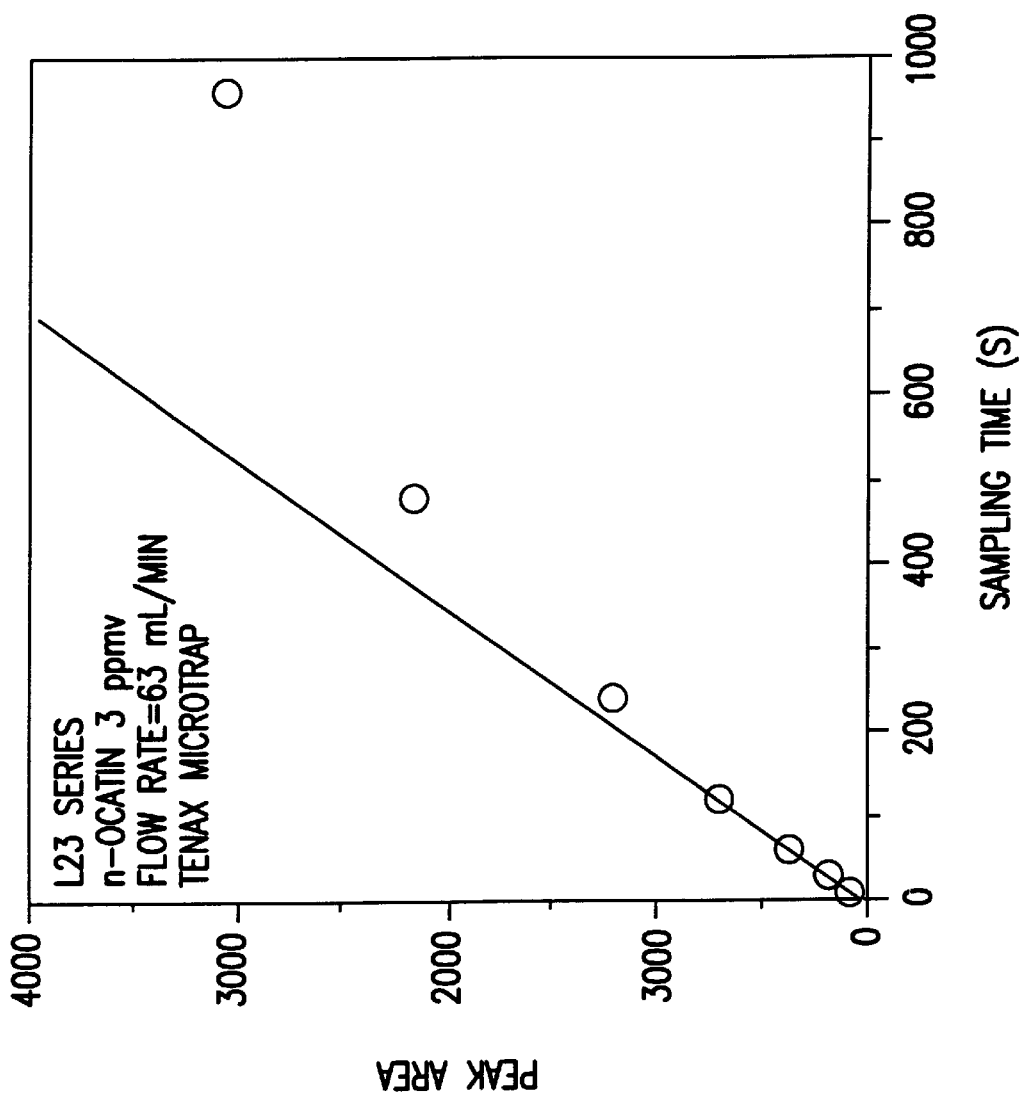
FIG. 13 is a diagram showing quantitative preconcentration of a volatile compound received by the preconcentrator assembly of the present invention using the trap breakthrough data.

Quantitative preconcentration of a volatile compound using the valveless preconcentrator assembly 12 is demonstrated using the trap "breakthrough" data shown in FIG. 13. In these tests, a standard consisting of 3 parts per million n-octane vapor in air was sampled onto a Tenax filled sorbent tube in the valveless preconcentrator assembly of the present invention for varying amounts of time and then desorbed and analyzed using a flame ionization detector. A 10 m×0.18 mm i.d. DB-1 GC column was operated isothermally at 60° C. for the analysis. The sampling flow rate was approximately 60 mL/min and the trap was heated to 280° C. for desorption.

For sample times less than approximately 120 s, a linear relationship is observed between the sampling time and the peak area of the observed n-octane peak in the chromatograms. With longer sampling times, a systematic deviation is expected between the observed peak area and the sampling time as the sampled analytes begin themselves to elute through the trap. When the sample flow continues sufficiently long to carry compounds all the way through the trap, this process is referred to as "breakthrough". When breakthrough occurs, the trap approaches saturation and quantitation is lost as vapors are no longer fully retained on the trap. Different size beds, sorbent materials and operating temperatures can be used to effectively change the sampling capacity of a sorbent tube for a particular compound.

Figure 14:
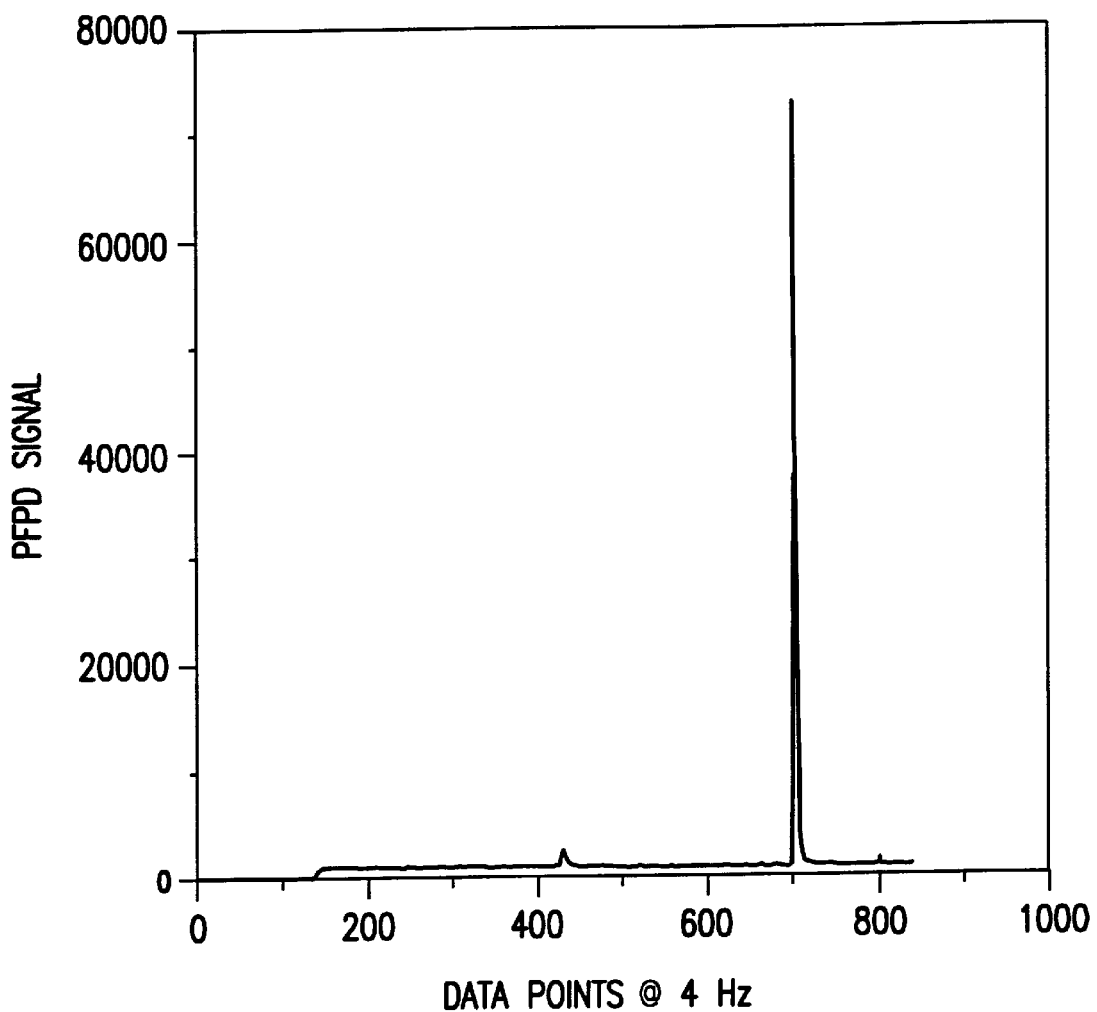
FIG. 14 is a diagram showing the results of chromatographic analysis of a liquid sample received within the preconcentrator assembly of the present invention; and, FIG. 15 is a diagram representing the resulting chromatogram running the identical method as the analysis in FIG. 14.

An example of a chromatographic analysis of a liquid sample using the preconcentrator assembly 12 is shown in FIG. 14. One microliter of a 100 $\mu$g/mL tributyl phosphate solution in methanol was directly injected using a microliter syringe into the preconcentrator containing a sorbent tube containing only a glass wool packing. The sorbent tube was thermally desorbed and vapors were injected to the GC just as if the preconcentrator had contained an adsorbent material.

Pulsed flame photometric detection at 4 Hz (i.e., 800 data points equals 200 s) shows initial quenching of the trace by the eluting solvent vapor followed by a later chromatographic peak for the tributyl phosphate. This separation was done with a temperature program of 1° C./s of a 10 m×0.18 mm DB-1 fused silica capillary column with pressure programming for constant flow of approx. 1.2 mL/min.

Following this analysis, the sorbent tube was heated to the same desorbing temperature, 220° C., while the trap housing was positioned at the instrument inlet and carrier gas was flown through the trap for 60 s to clean the trap. This operation is commonly referred to as a "baking" or "bakeout" operation.

Figure 15:
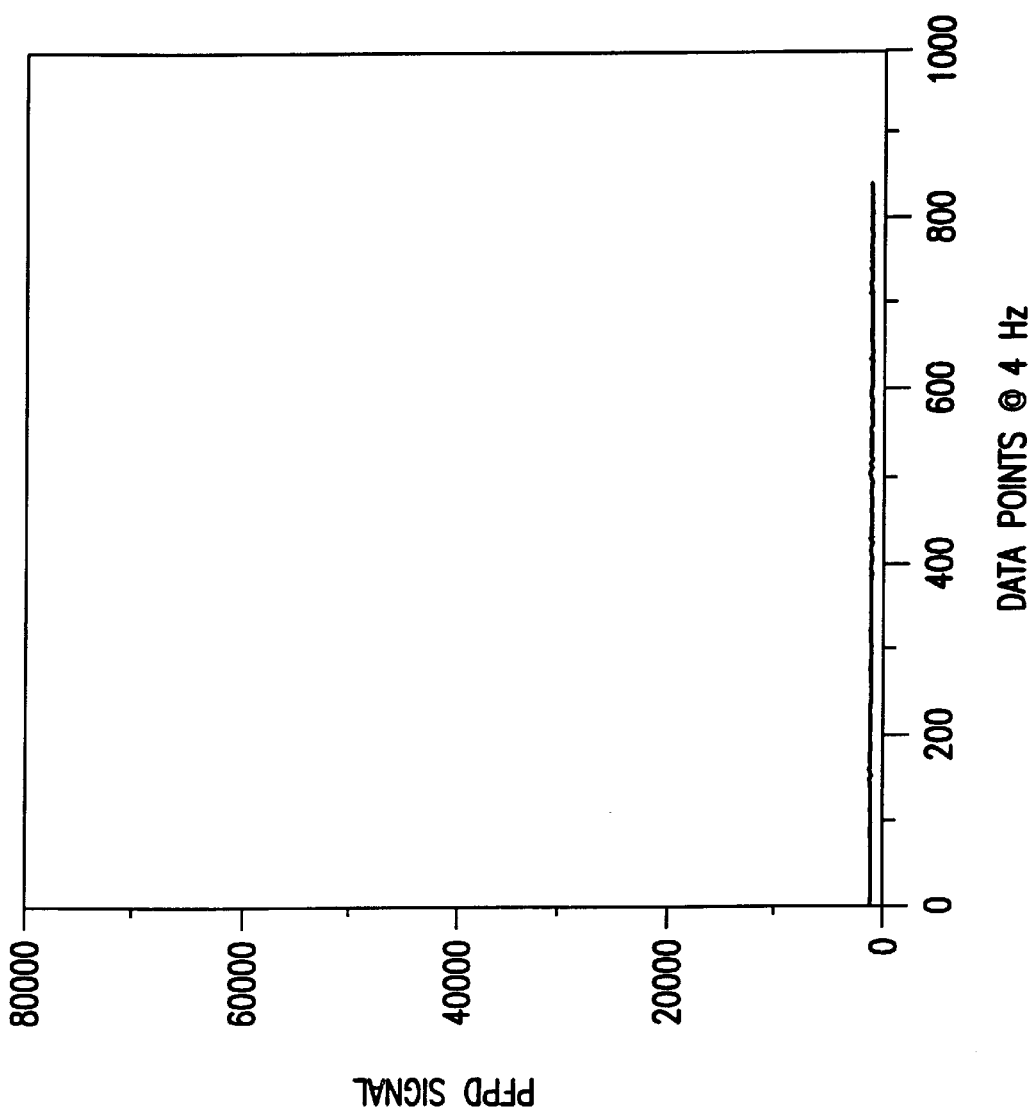

Following this operation, the preconcentrator was again closed and any thermally generated vapors were injected directly into the gas chromatograph. The resulting chromatogram running the identical method as the analysis in FIG. 14 is shown in FIG. 15. A flat baseline with no observable carryover of tributyl phosphate from the previous analysis is observed. This demonstrates the versatility of the valveless preconcentrator assembly of the present invention to handle commonly encountered liquid samples which are not normally processed using thermal desorption instrumentation. In fact, the programmable nature of the valveless preconcentrator readily allows time-dependent heating profiles to be carried out. This can be applied to solid materials to measure temperature dependent vapor release, for example.

In another application for solvent sensitive detectors, liquid samples can be heated at a suitable temperature sufficient to drive off solvent before the preconcentrator is closed. In the example shown in FIG. 14, the initial quenching of the baseline could be largely eliminated by initial removal of the solvent before injection using this type of approach.

One other way the valveless preconcentrator assembly 12 could be used is leaving the sorbent out, and using it to sample and inject known volumes (the volume of the empty sorbent tube) of air for analysis.

By timing the injection and setting the flow rate (controlling the pressure), the volume injected onto the GC is known and the GC can provide a direct analysis of the air. GCs used for manufacturing process control in industry often take fixed volume samples respectively for monitoring gas composition using valves that switch through a tubing loop of known volume, and when ready for injection, this loop is valve-switched into the flow stream of the GC.

The system of the present invention may do this without having to pass the gas sample through the valve as it just goes into the opened apparatus, fills an empty preconcentrator tube, and the apparatus closes and injects a known volume.

It is shown that a new valveless, low power, ambient temperature, flexible vapor sampling system have been reduced to practice in which an in-line trap mechanically opens directly to the media surrounding the device for sample introduction and then seals to a fitting for thermal desorption and vapor injection into an analyzer system.

Both gaseous and liquid samples introduced into this system are easily analyzed. The opening in the trap housing makes it easy to remove and exchange sorbent tubes when needed. The trap housing has many degrees of motion added to it, so that it is capable of sliding reciprocating motion as well as rotation along a needed trajectory.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described. Certain features may be used independently of other features, and in certain cases, particular locations of elements may be reversed or interposed, all without departing from the spirit or scope of the invention as defined in the appended Claims.

What is claimed is:

1. A system for vapor constituents analysis of a media, comprising:
   a gas chromatographic column, and
   an in-line preconcentrator assembly having a sampling mode of operation and an injection mode of operation; said preconcentrator assembly including:
      (a) a trap housing identifying a media receiving compartment formed internally therein,
      (b) an adsorbent material removably received within said media receiving compartment, and
      (c) a transfer line unit removably couplable to said trap housing at a first end thereof, said transfer line unit being directly connected to said gas chromatographic column;
   wherein, in said sampling mode of operation of said preconcentrator assembly, said trap housing being displaced from said transfer line unit, whereby a direct fluid communication path is established between the media and said media receiving compartment within said trap housing;
   wherein, in said injection mode of operation of said preconcentrator assembly, said trap housing being positioned in the pressure tight engagement with said transfer line unit, whereby fluid communication is established between said media receiving compartment within said trap housing and said gas chromatographic column through said transfer line unit.

2. The system of claim 1, further including carrier means for repositioning said trap housing with respect to said transfer line unit.

3. The system of claim 1, wherein said trap housing reciprocates with respect to said transfer line unit.

4. The system of claim 1, wherein said trap housing moves along an arc trajectory with respect to said transfer line unit.

5. The system of claim 2, further including controlling means controlling said carrier means.

6. The system of claim 1, wherein said media is a gaseous media.

7. The system of claim 1, wherein said media is a liquid media.

8. The system of claim 1, further including a sample pump connected to a second end of said trap housing through a sample pump valve, said sample pump being actuated and said sample pump valve being opened during said sampling mode of operation of said preconcentrator assembly, thereby forcing the media to enter into said media receiving compartment.

9. The system of claim 1, further including a carrier gas supply connected to a second end of said trap housing and providing a flow of the carrier gas through said media receiving compartment towards said gas chromatographic column during said injection mode of operation of said preconcentrator assembly.

10. The system of claim 9, further including means for desorbing the vapor constituents of the media from said adsorbent material into the flow of the carrier gas.

11. The system of claim 1, wherein said preconcentrator assembly further has a desorbing mode of operation succeeding said sampling mode of operation and timely coinciding with said injection mode of operation, said system further comprising means for heating said adsorbent material during said desorbing mode of operation in the presence of a carrier gas stream flowing past said adsorbent material towards said gas chromatographic column.

12. The system of claim 1, wherein said adsorbent material is encased in a sorbent tube.

13. The system of claim 12, wherein said trap housing includes a trap body member having a proximal end and a distal end, and a trap end member threadingly and removably engaging said trap body member at said distal end thereof, an axial channel extending longitudinally through said trap body member and said trap end member substantially entire lengths thereof,
   said sorbent tube being disposed along said axial channel with said adsorbent material being disposed within said sorbent tube in a part thereof extending within said trap body member,
   a heater wire being wound around said sorbent tube along said part thereof extending within said trap body member, and
   a heater wire support tube extending coaxialy with said sorbent tube substantially the length of said trap body member and disposed between said heater wire and said sorbent tube, said heater wire support tube being insulated from said heater wire.

14. The system of claim 13, further including sealing O-rings disposed between internal walls of said trap housing and said sorbent tube.

15. The system of claim 13, wherein said proximal end of said trap body member has a conical shape.

16. The system of claim 13 wherein said transfer line unit includes:
- a cylindrical body having a longitudinal channel and a front end facing said proximal end of said trap body member of said trap housing, a cylindrical recess being formed in said front end of said cylindrical body, said proximal end of said trap body member being received within said recess;
- a capillary transfer line extending along said longitudinal channel and maintained in position by a face O-ring positioned within said longitudinal channel at said recess in said front end of said cylindrical body,
- a heater wire being wound around said capillary transfer line and extending within said longitudinal channel, and
- a temperature sensor sensing said heater wire.

17. The system of claim 1, further including an analyzer connected to said gas chromatographic column.

18. The system of claim 2, wherein said carrier means includes a Rohlix clutch.

19. The system of claim 5, wherein said carrier means is driven by a DC motor, and wherein said controlling means provides a first DC voltage to said DC motor for driving said trap housing towards said transfer line unit, and a second DC voltage for reverse movement, said first DC voltage being smaller than said second DC voltage.

20. The system of claim 2, further including a first motor for sliding said trap housing, and a second motor for driving said trap housing along an arc trajectory.

21. The system of claim 5, wherein said controlling means includes computer interface and valve driver interface.

22. The system of claim 11, wherein said means for heating said adsorbent material are controlled by controlling means.

23. The system of claim 16, wherein the temperature of said capillary transfer line is controlled by controlling means.

24. A method of vapor constituents analysis, comprising the steps of:
  providing a gas chromatographic column, connecting an analyzer to said gas chromatographic column at one end thereof, providing an in-line preconcentrator assembly including:
    (a) a trap housing having a media receiving compartment,
    (b) a transfer line unit connected to said gas chromatographic column at another end thereof, and
    (c) carrier means for repositioning said trap housing with respect to said transfer line unit;
  connecting a sampling pump and carrier gas supply to said trap housing;
  displacing said trap housing from said transfer line unit by means of said carrier means;
  positioning a sorbent tube into said media receiving compartment;
  activating said sampling pump, thereby establishing a directed flow of a media surrounding said trap housing into said media receiving compartment therein,
  moving said trap housing by means of said carrier means towards said transfer line unit, and providing pressure tight engagement therebetween,
  activating said carrier gas supply thereby establishing a stream of the carrier gas flowing past said sorbent tube towards said gas chromatographic column,
  heating said sorbent tube, thereby releasing the vapor constituents into the carrier gas stream, and
  heating said transfer line unit.

25. The method of claim 24, wherein said sorbent tube and said gas chromatographic column are ramp heated during desorption.

26. The method of claim 24, wherein said transfer line unit is maintained at an isothermal temperature.

27. The method of claim 24, further including the steps of:
  driving said carrier means by means of a DC motor,
  providing a reduced DC voltage to said DC motor during movement of said trap housing towards said transfer line unit, and
  providing a DC voltage larger than said reduced DC voltage during displacing said trap housing from said transfer line unit.

28. The method of claim 24, further including the steps of:
  providing a first motor and a second motor, driving said trap housing linearly displacing the same from said transfer line unit a first predetermined distance by means of said first motor,
  rotating said trap housing 180° by means of said second motor,
  linearly driving said trap housing towards a sampling source by means of said first motor a second predetermined distance,
  sampling said media,
  retracting said trap housing from said sampling source by said first motor, rotating said trap housing 180° by said second motor, and
  linearly moving said trap housing towards said transfer line unit said first predetermined distance by said first motor.

\* \* \* \* \*